(12) United States Patent
Alchas et al.

(10) Patent No.: US 6,843,781 B2
(45) Date of Patent: Jan. 18, 2005

(54) INTRADERMAL NEEDLE

(75) Inventors: Paul G. Alchas, Wayne, NJ (US); Philippe Emile Fernand Laurent, Oullins (FR); Carlos E. Guillermo, Clinton, CT (US); Marina S. Korisch, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/834,438

(22) Filed: Apr. 13, 2001

(65) Prior Publication Data

US 2002/0068909 A1 Jun. 6, 2002

Related U.S. Application Data

(63) Continuation-in-part of application No. 09/417,671, filed on Oct. 14, 1999.

(51) Int. Cl.$^7$ ................................................ A61M 5/00
(52) U.S. Cl. ...................................................... 604/117
(58) Field of Search .......................... 604/46–47, 93.01, 604/116–117, 181, 182, 187, 188, 192, 198, 207, 228, 232, 234, 240–242; 128/919; 206/210, 571, 363, 438; 220/4.01, 4.04–4.07

(56) References Cited

U.S. PATENT DOCUMENTS

| | | | | |
|---|---|---|---|---|
| 1,934,046 A | * | 11/1933 | Demarchi | 604/115 |
| 2,876,770 A | | 3/1959 | White | 128/215 |
| 3,073,306 A | | 1/1963 | Linder | 128/215 |
| 3,400,715 A | | 9/1968 | Pederson | 128/215 |
| 4,373,526 A | | 2/1983 | Kling | 604/117 |
| 4,468,223 A | | 8/1984 | Minagawa et al. | 604/199 |
| 4,769,003 A | | 9/1988 | Stamler | 604/39 |
| 4,774,948 A | * | 10/1988 | Markham | 606/185 |
| 4,834,704 A | * | 5/1989 | Reinicke | 604/506 |
| 4,883,473 A | | 11/1989 | Thomas | |
| 4,898,588 A | | 2/1990 | Roberts | 604/187 |
| 4,955,871 A | | 9/1990 | Thomas | |
| 4,978,344 A | | 12/1990 | Dombrowski et al. | 604/198 |
| 5,137,516 A | | 8/1992 | Rand et al. | 604/136 |
| 5,141,496 A | * | 8/1992 | Dalto et al. | 604/117 |
| 5,147,328 A | * | 9/1992 | Dragosits et al. | 222/386 |
| 5,190,521 A | | 3/1993 | Hubbard et al. | 604/51 |
| 5,195,526 A | * | 3/1993 | Michelson | 600/431 |
| 5,222,949 A | | 6/1993 | Kaldany | |
| 5,417,662 A | | 5/1995 | Hjertman et al. | 604/117 |
| 5,578,014 A | | 11/1996 | Erez et al. | 604/192 |
| 5,672,883 A | * | 9/1997 | Reich | 206/365 |

(List continued on next page.)

FOREIGN PATENT DOCUMENTS

| | | |
|---|---|---|
| DE | 41 27 887 C1 | 1/1993 |
| DE | 29918794 | 2/2000 |

(List continued on next page.)

Primary Examiner—LoAn H. Thanh
(74) Attorney, Agent, or Firm—David M. Fortunato

(57) ABSTRACT

An intradermal needle assembly that is attachable to a prefillable container intended for intradermally injecting substances into an animal includes a needle cannula supported by a hub portion. The hub portion is adapted to receive the prefillable container just prior to administering the intradermal injection. A limiter portion surrounds the needle cannula and extends away from the hub portion toward a forward tip of the needle cannula, and includes a skin engaging surface with the needle cannula having a fixed angle of orientation, preferably generally perpendicular, relative to the plane of the skin engaging surface. The skin engaging surface is received against the skin of an animal to administer an intradermal injection. The forward tip extends beyond the skin engaging surface a distance enabling penetration of the needle cannula into the dermis layer of the skin of the animal enabling injection of the substance into the dermis layer.

15 Claims, 7 Drawing Sheets

U.S. PATENT DOCUMENTS

| | | | |
|---|---|---|---|
| 5,873,856 A * | 2/1999 | Hjertman et al. | 604/117 |
| 5,921,963 A | 7/1999 | Erez et al. | 604/192 |
| 6,099,504 A * | 8/2000 | Gross et al. | 604/140 |
| 6,200,291 B1 * | 3/2001 | Di Pietro | 604/117 |
| 6,210,369 B1 | 4/2001 | Wilmot et al. | 604/157 |

FOREIGN PATENT DOCUMENTS

| | | |
|---|---|---|
| EP | 0 904 790 A2 | 3/1999 |
| EP | 1066848 | 1/2001 |
| EP | 1092444 | 4/2001 |
| GB | 735538 | 8/1955 |
| GB | 2 206 794 A | 1/1989 |
| JP | 2000-37456 | 2/2000 |
| WO | 9309826 | 5/1993 |
| WO | WO 95/01198 | 1/1995 |
| WO | 9925402 | 5/1999 |
| WO | WO 99/27986 | 6/1999 |
| WO | 0056384 | 9/2000 |

* cited by examiner

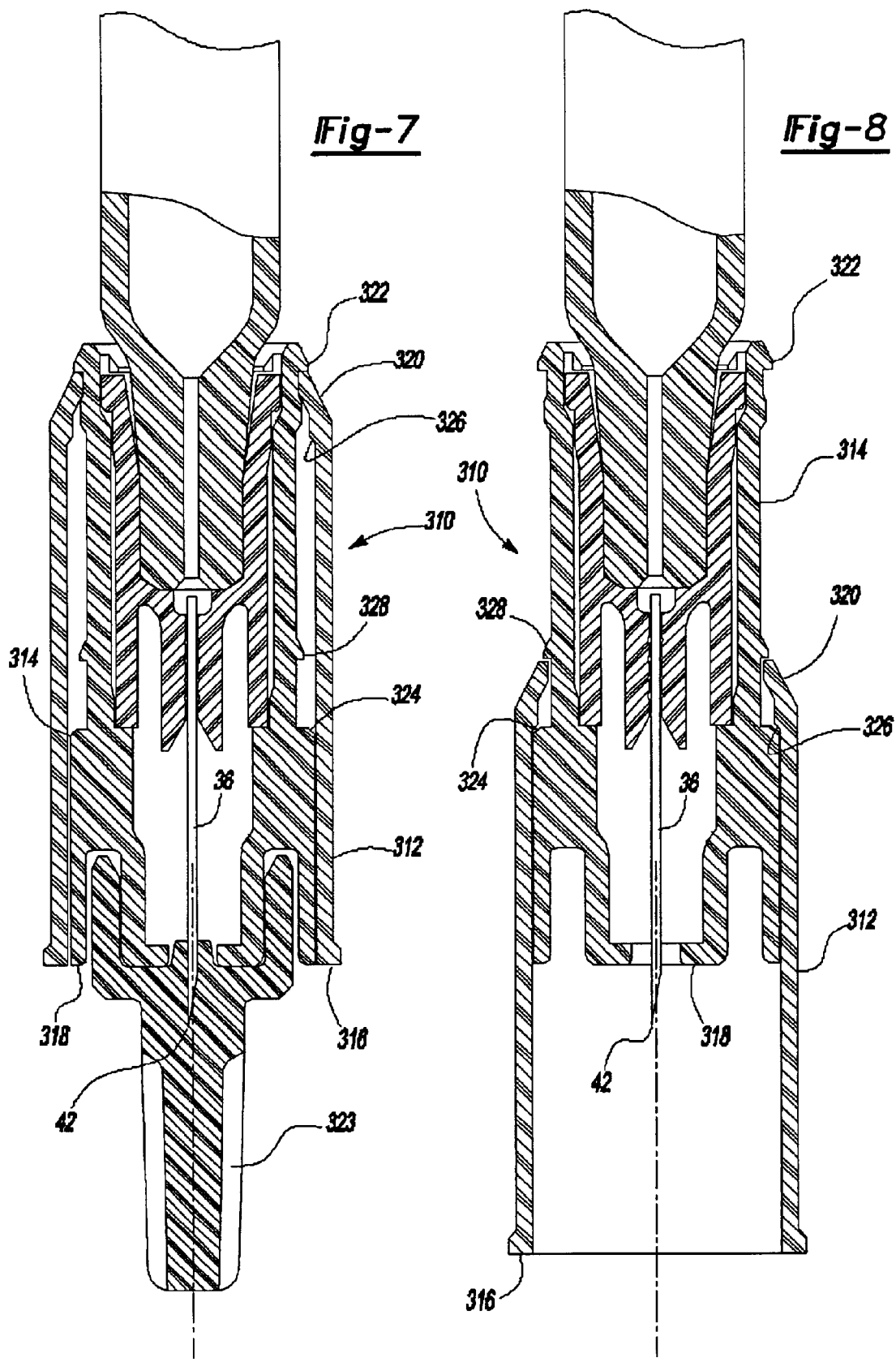

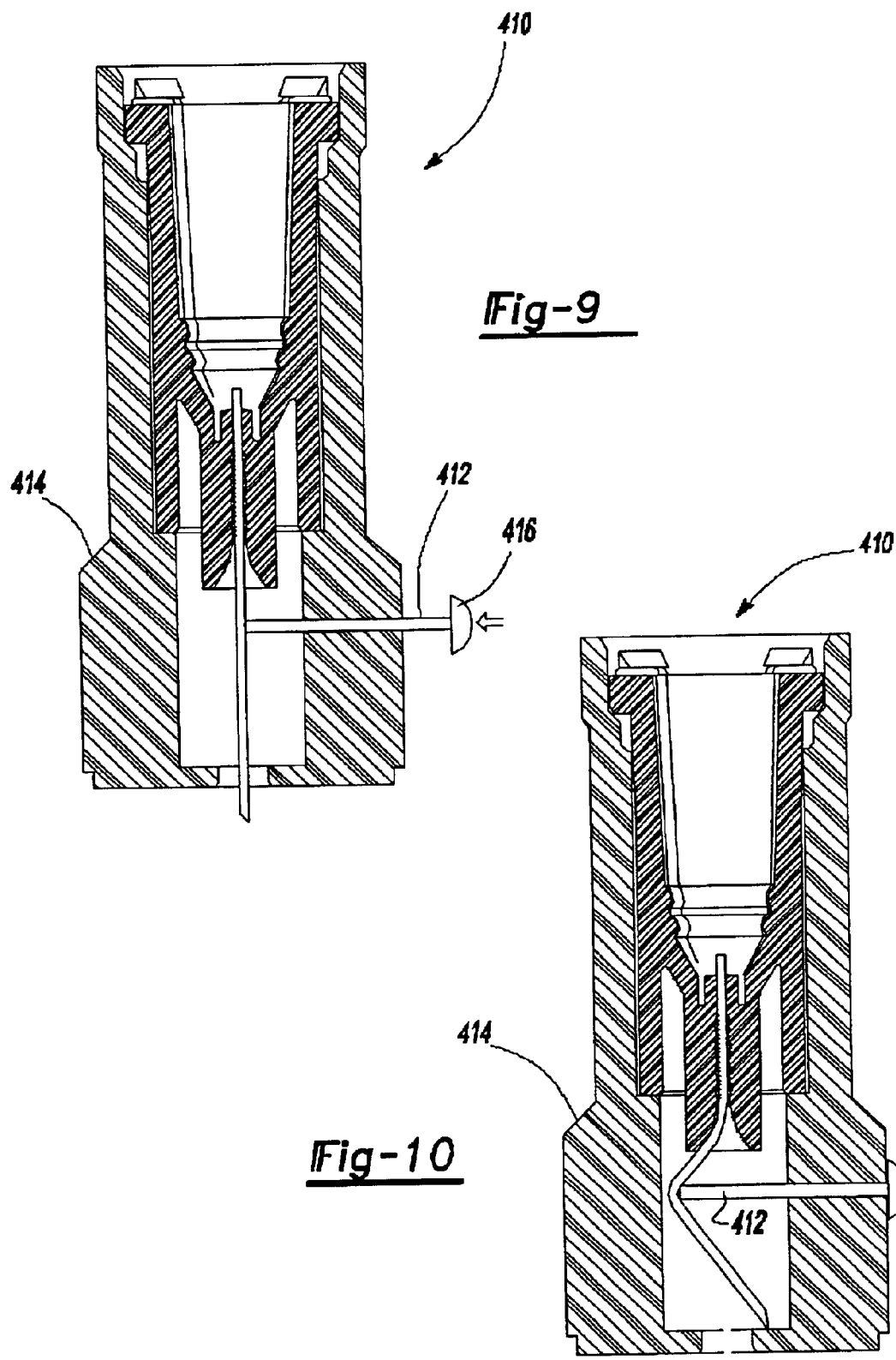

INTRADERMAL NEEDLE

The present application is a continuation-in-part of U.S. patent application Ser. No. 09/417,671, filed on Oct. 14, 1999.

FIELD OF THE INVENTION

The present invention generally relates to a needle assembly attachable to a prefillable container for delivering substances such as drugs, vaccines and the like used in the prevention, diagnosis, alleviation, treatment, or cure of disease into the skin of an animal using an injection device having a needle cannula and a limiter for engaging the surface of the skin and limiting penetration of the tip of the needle cannula into the skin. Preferably, the limiter limits penetration of the needle cannula from approximately 1.0 mm to approximately 2.0 mm, and most preferably around 1.5 mm±0.2 mm to 0.3 mm, such that the substance is injected into the dermis layer of the animal. The orientation of the needle cannula is fixed so that the needle cannula is preferably generally perpendicular to the plane of the skin engaging surface of the limiter within about fifteen degrees or more preferably ninety degrees within about five degrees, and the skin engaging surface is generally flat.

BACKGROUND OF THE INVENTION

Intradermal injections are used for delivering a variety of substances. Many of these substances have proven to be more effectively absorbed into or react with the immune response system of the body when injected intradermally. Recently, clinical trials have shown hepatitis B vaccines administered intradermally are more imunogenic than if administered intramuscularly. In addition, substances have been injected intradermally for diagnostic testing, such as, for example using what is known in the art as the "Mantoux test" to determine the immunity status of the animal against tuberculosis and the immediate hypersensitivity status of Type I allergic diseases. It is desirable, in some instances, to provide a prefilled container filled with one of these substances and to mate the needle cannula to the container just prior to administering the injection.

An intradermal injection is made by delivering the substance into the epidermis and upper layer of the dermis. Below the dermis layer is subcutaneous tissue (also sometimes referred to as the hypodermis layer) and muscle tissue, in that order. There is considerable variation in the skin thickness both between individuals and within the same individual at different sites of the body. Generally, the outer skin layer, epidermis, has a thickness between 500–200 microns, and the dermis, the inner and thicker layer of the skin, has a thickness between 1.5–3.5 mm. Therefore, a needle cannula that penetrates the skin deeper than about 3.0 mm has a potential of passing through the dermis layer of the skin and making the injection into the subcutaneous region, which may result in an insufficient immune response, especially where the substance to be delivered intradermally has not been indicated for subcutaneous injection. Also, the needle cannula may penetrate the skin at too shallow a depth to deliver the substance and result in what is commonly known in the art as "wet injection" because of reflux of the substance from the injection site.

Due to the inherent limitations of the standard needle assembly, the standard procedure for making an intradermal injection is known to be difficult to perform, and therefore dependent upon experience and technique. This procedure is recommended to be performed by stretching the skin, orienting the needle bevel to face upwardly, and inserting a 26 Gauge short bevel needle cannula to deliver a volume of 0.5 ml or less of the substance into the skin of an animal with the needle cannula being inserted into the skin at an angle varying from around 10–15 degrees to form a blister or wheal in which the substance is deposited or otherwise contained. Accordingly, the technique utilized to perform the standard intradermal injection is difficult and requires the attention of a trained nurse or medical doctor. Inserting the needle to a depth greater than about 3.0 mm typically results in a failed intradermal injection because the substance being expelled through the cannula will be injected into the subcutaneous tissue of the animal.

The most frequent cause of a failed intradermal injection is derived from inserting the needle into the skin at an angle greater than 15 degrees relative to the flattened skin surface. A further cause of error is derived from pinching rather than stretching the skin in the area of the injection, which is normally done when giving a subcutaneous rather than an intradermal injection. Pinching increases the likelihood of giving a subcutaneous injection. Procedural errors as described above result in delivering the contents of the injection into the subcutaneous layer, which can reduce the effectiveness of the injection, as well as possibly deliver the substance in a way not approved for delivery. Intradermal injections performed by using the standard procedure also are known to cause a significant amount of pain to the recipient of the injection because the needle cannula is inserted into the skin at an angle of about fifteen degrees. By inserting the needle cannula at this angle, about 5 mm to about 6 mm of the needle is actually inserted into the skin. This results in a significant disruption of the pain receptors dispersed throughout the upper layers of the skin. Also, self-administered intradermal injections are not possible using the present method.

Accordingly, there has been a long felt need for a needle assembly attachable to a prefillable container enabling a simplified method of performing an intradermal injection of substances which overcomes the problems and limitations associated with the use of conventional devices, especially reducing the probability of error and pain caused from the injection by making such injections less dependent upon experience and technique. In addition, there has been a need to reliably limit the depth of penetration of the needle cannula into the skin of the animal to avoid entry into the subcutaneous layer of the skin as well as reliably fix the orientation of the needle cannula relative to the skin. Also, there has been a need to apply pressure to the skin of the animal to facilitate formation of the blister or wheal in the skin in which the substance is deposited or otherwise contained and avoid wet injections. Further, pressure is applied to mask the pain derived from the intradermal injection by stimulating the muscle fibers to block the pain receptors. Still further, there has been a need to provide an needle assembly capable of addressing each of these shortcomings and yet be mated to the prefilled container just prior to administering the injection.

SUMMARY OF THE INVENTION AND ADVANTAGES

In contrast to the conventional needle assembly and delivery method discussed above, it has been found by the applicant that intradermally injecting substances into the skin can be performed in connection with the use of the present invention to effectively and reliably deliver such substances intradermally.

The intradermal needle assembly of the present invention for use with a prefillable container having a reservoir capable of storing a substance for injection into the skin of an animal includes a hub portion being attachable to the prefillable container storing the substance, a needle cannula supported by the hub portion and having a forward tip extending away from the hub portion, and a limiter portion surrounding the needle cannula and extending away from the hub portion toward the forward tip of the needle cannula, the limiter including a generally flat skin engaging surface extending in a plane generally perpendicular to an axis of the needle cannula and adapted to be received against the skin of the animal to administer an intradermal injection of the substance, the needle forward tip extending beyond the skin engaging surface a distance approximately 0.5 mm to 3.0 mm wherein the limiter portion limits penetration of the needle into the dermis layer of skin of the animal so that the vaccine is injected into the dermis layer of the animal.

In the preferred embodiment of the assembly, the plane is generally perpendicular to the axis of the needle cannula within about five degrees. In addition, the hub portion and the limiter portion are formed as separate pieces, with the limiter portion defining an inner cavity receiving at least a portion of the hub and including an abutment engaging a corresponding structure on the hub portion thereby limiting the length of the needle cannula extending beyond the skin engaging surface. Also, the hub portion includes a throat for receiving the prefillable container, with the needle cannula fixedly attached to the hub portion, preferably with an adhesive including an epoxy curable with ultra violet light. The limiter portion includes a plurality of snaps engaging the hub portion thereby fixedly attaching the hub portion to the limiter portion.

Also, in the preferred embodiment of the assembly, the limiter portion and the hub portion are integrally formed as a single component, with the needle cannula fixedly attached to the hub portion of the single component behind the skin engaging surface of the limiter portion, with the hub portion including a throat for receiving the prefillable container and with the needle cannula fixedly attached to the hub portion with an adhesive. In addition, the skin engaging surface comprises a rigid polymer having an elastomeric central area with the needle cannula extending therethrough. Further, the substance includes an influenza vaccine. Still further, the needle assembly is attachable to a prefillable container with a Luer fit.

In addition, the assembly further includes a sleeve circumscribing the limiter and being slidable for shielding the forward tip subsequent to administering an intradermal injection, with the limiter including at least one ramp allowing the limiter to be moved toward the forward tip and preventing the limiter from being moved away from the forward tip upon shielding the forward tip. Also, a tip cap is removably affixed to the skin engaging surface and has the forward tip received therein. The limiter includes a needle plunger slidably received thereby and is oriented generally perpendicular to the axis of the needle cannula within about fifteen degrees. The needle plunger is depressable thereby bending the needle cannula and retracting the needle cannula into the limiter for shielding the forward tip subsequent to administering an injection. Further, the skin engaging surface includes an outer diameter of at least 5 mm. The preferred embodiment of the assembly further includes a forward cap being matable to a rearward cap wherein the caps enclose the needle assembly therebetween, with the forward cap and the rearward cap forming a sterile enclosure for storing the needle assembly.

Alternatively, the intradermal needle assembly of the present invention for use with a prefillable container having a reservoir capable of storing a substance for injection into the skin of an animal includes a hub portion having a throat for receiving the prefillable container, a needle cannula being supported by the hub portion and having a forward tip extending away from the hub portion, and a limiter portion surrounding the hub portion and the needle cannula and extending away from the hub portion toward the forward tip of the needle, the limiter portion including a generally flat skin engaging surface extending in a plane generally perpendicular to an axis of the needle cannula and being adapted to be received against the skin of an animal to receive an intradermal injection of a vaccine, and the forward tip extending beyond the skin engaging surface from approximately 0.5 mm to approximately 3.0 mm wherein the limiter portion limits penetration of the needle cannula into the dermis layer of the skin of the animal thereby injecting the substance into the dermis layer of the animal.

In the preferred embodiment, the hub portion and the limiter portion are formed as separate pieces, with the limiter portion defining an inner cavity receiving at least a portion of the hub and including an abutment engaging a corresponding structure on the hub portion thereby limiting the length of the needle cannula extending beyond the skin engaging surface. Also, needle cannula is fixedly attached to the hub portion preferably with an adhesive including an epoxy curable with ultra violet light.

Also, the limiter portion includes a plurality of snaps engaging the hub portion thereby fixedly attaching the hub portion to the limiter portion. In addition, the limiter portion and the hub portion are integrally formed as a single component, with the needle cannula preferably fixedly attached to the hub portion of the single component behind the skin engaging surface of the limiter portion.

In addition, in the preferred embodiment, the skin engaging surface comprises a rigid polymer having an elastomeric central area with the needle cannula extending therethrough, and needle assembly is attachable to a prefillable container with a Luer fit. Also, a sleeve circumscribes the limiter and is slidable for shielding the forward tip subsequent to administering an intradermal injection, with the limiter including at least one ramp allowing the limiter to be moved toward the forward tip and preventing the limiter from being moved away from the forward tip upon shielding the forward tip. The assembly may also include a tip cap removably affixed to the skin engaging surface and having the forward tip received therein. Further, the limiter may include a needle plunger slidably received thereby and oriented generally perpendicular to the axis of the needle cannula, with the needle plunger preferably depressable thereby bending the needle cannula and retracting the needle cannula into the limiter for shielding the forward tip subsequent to administering an injection. In addition, a forward cap is matable to a rearward cap wherein the caps enclose the needle assembly therebetween, with the forward cap and the rearward cap forming a sterile enclosure for storing the needle assembly.

Alternatively, the intradermal needle assembly of the present invention attachable to a prefillable container having a reservoir adapted to contain a substance for use in intradermally injecting vaccines into the skin of an animal, includes a needle cannula affixed to a hub portion and being in fluid communication with the outlet port, the needle having a forward tip that is adapted to penetrate an the skin of an animal, and a limiter surrounding the needle cannula and having a generally flat skin engaging surface extending in a plane ranging between five and fifteen degrees from perpendicular to an axis of the needle cannula and being adapted to be placed against the skin of the animal to administer an intradermal injection of the substance, the needle forward tip extending away from the skin engaging surface from approximately 0.5 mm to approximately 3.0 mm such that the limiter limits penetration of the forward tip into the dermis layer of the skin of an animal so that the substance is injected into the dermis layer of the skin.

In the preferred embodiment of the assembly, the hub portion and the limiter portion are formed as separate pieces, with the limiter portion defining an inner cavity receiving at least a portion of the hub and including an abutment engaging a corresponding structure on the hub portion thereby limiting the length of the needle cannula extending beyond the skin engaging surface.

In yet another embodiment of the intradermal needle assembly of the present invention for use with a prefillable container having a reservoir capable of storing a substance for injection into the skin of an animal, the assembly includes a hub portion being attachable to the prefillable container storing the substance, a needle cannula supported by the hub portion and having a forward tip extending away from the hub portion, a limiter portion surrounding the needle cannula and extending away from the hub portion toward the forward tip of the needle cannula, the limiter including a generally flat skin engaging surface extending in a plane generally perpendicular to an axis of the needle cannula and adapted to be received against the skin of the animal to administer an intradermal injection of the substance, the needle forward tip extending beyond the skin engaging surface a distance approximately 0.5 mm to 3.0 mm wherein the limiter portion limits penetration of the needle into the dermis layer of skin of the animal so that the vaccine is injected into the dermis layer of the animal, and an enclosure means for concealing the needle cannula following injection.

In the preferred embodiment, the enclosure means comprises the limiter being slideably disposed about the needle cannula and having at least a first position and a second position, the first position exposing the forward tip of the needle cannula and the second position concealing the forward tip of the needle cannula, with the limiter preferably defining at least one slot oriented generally parallel to the needle cannula and having a protuberance disposed on one side thereof. Also, the assembly includes a hub supporting the needle cannula and the hub including at least one locking finger and at least one stop, the at least one locking finger being cantilevered away from the forward tip and the at least one stop being cantilevered toward the forward tip, with the at least one locking finger including a tab received by the slot disposed in the limiter. The tab is snappable over the protuberance for moving the limiter from the first position to the second position, with the protuberance is disposed between the tab and the at least one stop when the limiter is located in the first position. The limiter may include a catch engaging the at least one stop when the limiter is in the second position thereby preventing the limiter from being moved into the first position from the second position.

In the preferred embodiment, the limiter comprises a non-elastomeric polymer, with the skin engaging surface including an elastomeric polymer being circumscribed by the non-elastomeric polymer. The elastomeric polymer may be pierced by the needle cannula when the limiter is mated to the hub portion. Also, the forward end the needle cannula includes a beveled tip ranging in length between approximately 0.8 mm and 1.0 mm, and approximately 0.9 mm. In addition, the enclosure means comprises a needle plunger inserted through the limiter and being depressable for bending the needle cannula thereby retracting the needle cannula into the limiter, with the needle plunger oriented generally perpendicular to the needle cannula. Further, a cap is attachable to the skin engaging surface for concealing the forward tip, with the cap comprising an elastomer and the forward tip insertable into the elastomer to thereby sealing the needle cannula and prevent the substance from leaking from the prefillable container through the cannula.

Also, the enclosure means comprises a tubular shield extendable from a retracted position to an extended position enclosing the needle cannula. In addition, the needle forward tip extends beyond the skin engaging surface about 1.0 to 2.0 mm, and preferably 1.5 mm±0.2 to 0.3 mm.

Also, the substance intradermally delivered in accordance with the method of the present invention is selected from the group consisting of drugs, vaccines and the like used in the prevention, diagnosis, alleviation, treatment, or cure of disease, with the drugs including Alpha-1 anti-trypsin, Anti-Angiogenesis agents, Antisense, butorphanol, Calcitonin and analogs, Ceredase, COX-II inhibitors, dermatological agents, dihydroergotamine, Dopamine agonists and antagonists, Enkephalins and other opioid peptides, Epidermal growth factors, Erythropoietin and analogs, Follicle stimulating hormone, G-CSF, Glucagon, GM-CSF, granisetron, Growth hormone and analogs (including growth hormone releasing hormone), Growth hormone antagonists, Hirudin and Hirudin analogs such as hirulog, IgE suppressors, Insulin, insulinotropin and analogs, Insulin-like growth factors, Interferons, Interleukins, Leutenizing hormone, Leutenizing hormone releasing hormone and analogs, Low molecular weight heparin, M-CSF, metoclopramide, Midazolam, Monoclonal antibodies, Narcotic analgesics, nicotine, Non-steroid anti-inflammatory agents, Oligosaccharides, ondansetron, Parathyroid hormone and analogs, Parathyroid hormone antagonists, Prostaglandin antagonists, Prostaglandins, Recombinant soluble receptors, scopolamine, Serotonin agonists and antagonists, Sildenafil, Terbutaline, Thrombolytics, Tissue plasminogen activators, TNF—, and TNF—antagonist, the vaccines, with or without carriers/adjuvants, including prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with, addiction, arthritis, cholera, cocaine addiction, diphtheria, tetanus, HIB, Lyme disease, meningococcus, measles, mumps, rubella, varicella, yellow fever, Respiratory syncytial virus, tick borne japanese encephalitis, pneumococcus, streptococcus, typhoid, influenza, hepatitis, including hepatitis A, B, C and E, otitis media, rabies, polio, HIV, parainfluenza, rotavirus, Epstein Barr Virus, CMV, chlamydia, non-typeable haemophilus, moraxella catarrhalis, human papilloma virus, tuberculosis including BCG, gonorrhoea, asthma, atheroschlerosis malaria, *E-coli*, Alzheimers, H. Pylori, salmonella, diabetes, cancer, herpes simplex, human papilloma and the like other substances including all of the major therapeutics such as agents for the common cold, Anti-addiction, anti-allergy, anti-emetics, anti-obesity, antiosteoporeteic, anti-infectives, analgesics, anesthetics, anorexics, antiarthritics, antiasthmatic agents, anticonvulsants, anti-depressants, antidiabetic agents, antihistamines, anti-inflammatory agents, antimigraine preparations, antimotion sickness preparations, antinauseants, antineoplastics, antiparkinsonism drugs, antipruritics, antipsychotics, antipyretics, anticholinergics, benzodiazepine antagonists, vasodilators, including general, coronary, peripheral and cerebral, bone stimulating agents, central nervous system stimulants, hormones, hypnotics, immunosuppressives, muscle relaxants, parasympatholytics, parasympathomimetrics, prostaglandins, proteins, peptides, polypeptides and other macromolecules, psychostimulants, sedatives, sexual hypofunction and tranquilizers and major diagnostics such as tuberculin and other hypersensitivity agents.

The present invention provides the desirable features set forth above that are not presently included together on the same needle assembly. The needle assembly allows an intradermal injection to be made at a generally perpendicular angle to the skin of the animal and also be attached to a prefilled container just prior to administering the intradermal injection. Further, the intradermal needle assembly of this invention may be used for self-administration of intradermal injections.

BRIEF DESCRIPTION OF THE DRAWINGS

Other advantages of the present invention will be readily appreciated as the same becomes better understood by reference to the following detailed description when considered in connection with the accompanying drawings wherein:

FIG. 7 is a side sectional view of a further alternative embodiment of the needle assembly showing a sleeve and a tip cap;

FIG. 8 is a side sectional view of the further alternative embodiment of the needle assembly showing the sleeve concealing the needle cannula;

FIG. 9 is a side sectional view of a further alternative embodiment of the needle assembly showing a needle plunger; and FIG. 10 is a side sectional view of the further alternative embodiment of the needle cannula showing the needle plunger retracting the needle cannula into the limiter.

DETAILED DESCRIPTION OF THE PREFERRED EMBODIMENT

Figures 1A, 2:
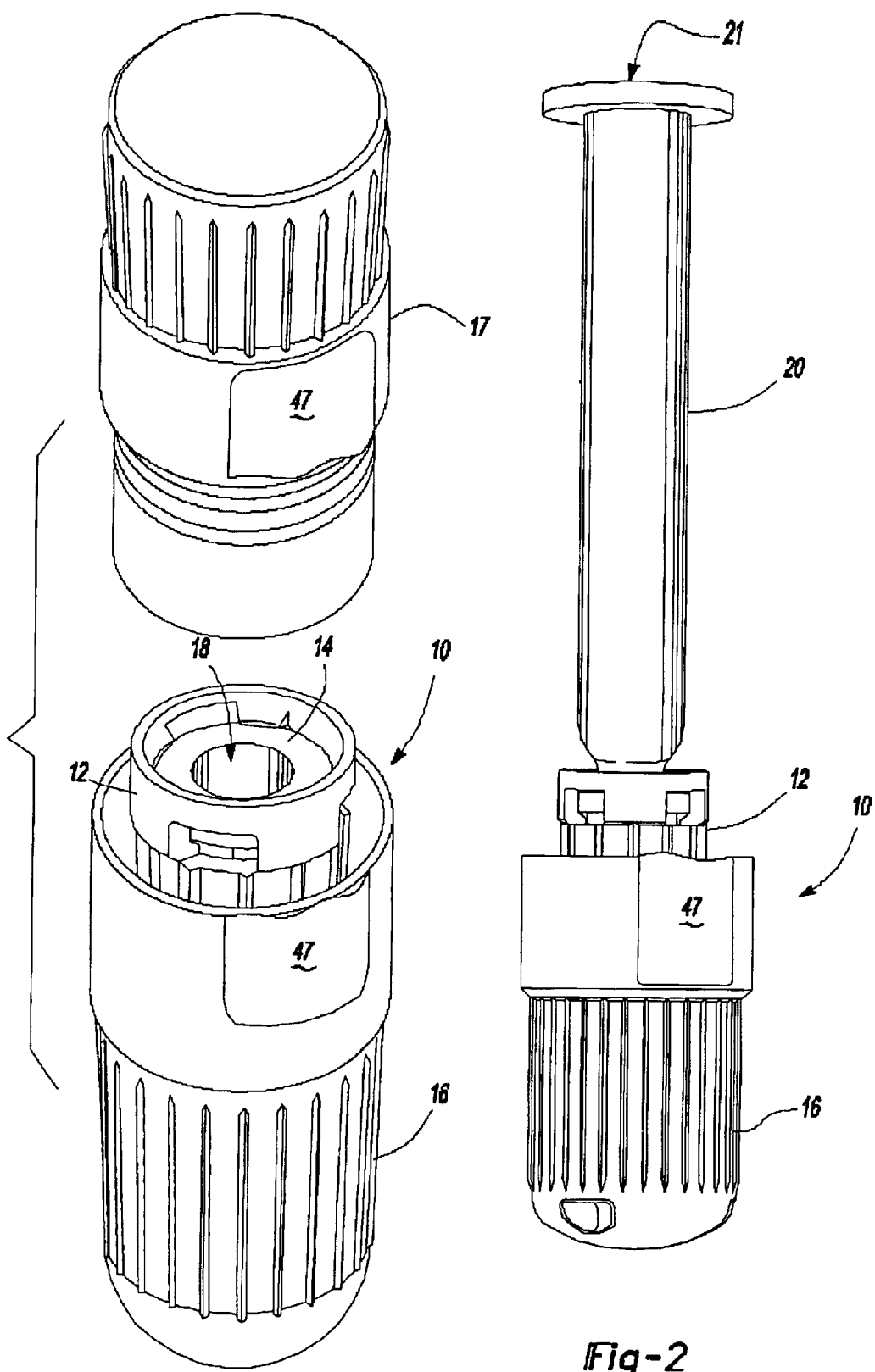
FIG. 1A is a partially exploded perspective view of the needle assembly of the present invention.
FIG. 2 is a perspective view of a prefillable container received by the needle assembly.
Figure 1B:
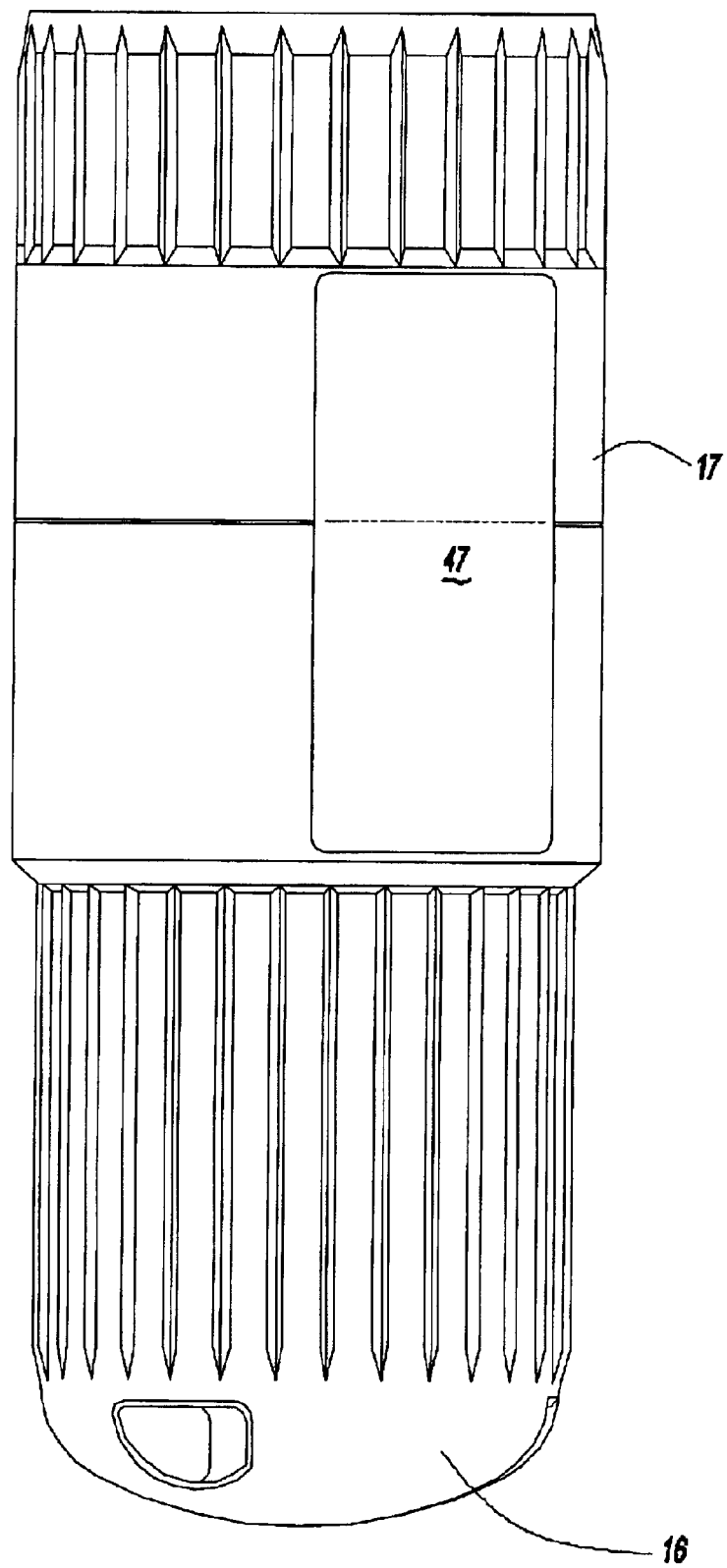
FIG. 1B is perspective view of the assembled caps of the needle assembly.

Referring to FIG. 1A and 1B, an intradermal needle assembly is generally shown at 10. The assembly includes a limiter portion 12 and a hub portion 14 disposed inside the limiter portion 12. A forward cap 16 is disposed upon the end of the hub portion 14, and a rearward cap 17 is removably affixed to the forward cap 16, the purpose of which will be explained further below. The hub portion 14 includes a throat 18 adapted to receive a prefillable container 20, as shown in FIG. 2.

The prefillable container 20 includes a reservoir 21 adapted to store substances intended for intradermal delivery into the skin of an animal. The substances comprise drugs or vaccines known to be absorbed into or react with the immune response system of the body significantly better in the dermis layer of the skin of the animal as opposed to in the subcutaneous or intramuscular region of the animal. Specifically, hepatitis B vaccines, it has been determined, are significantly more imunogenic when injected into the dermis layer of the skin of an animal. The prefillable container 20 may be a container that is filled at a pharmaceutical manufacturer with a liquid substance and sealed with a tip cap (not shown) for later use with the assembly 10 of the present invention. The prefillable container 20 may further be filled with a powder substance to which liquid is added just prior to administering the intradermal injection. Still further, the prefillable container may be filled with the entire substance just prior to administering the intradermal injection.

The prefillable container 20 can be any of a variety of designs such as, for example, a hypodermic syringe, cartridge, pen, and any other delivery device to which the assembly 10 may be attached that is designed to expel substances for injection into an animal. For example, the assembly 10 might include threads (not shown) for attachment to a pen. The prefillable container 20 represented in the figures is intended for demonstration purposes only and does not limit the scope of the subject needle assembly 10.

Figure 3:
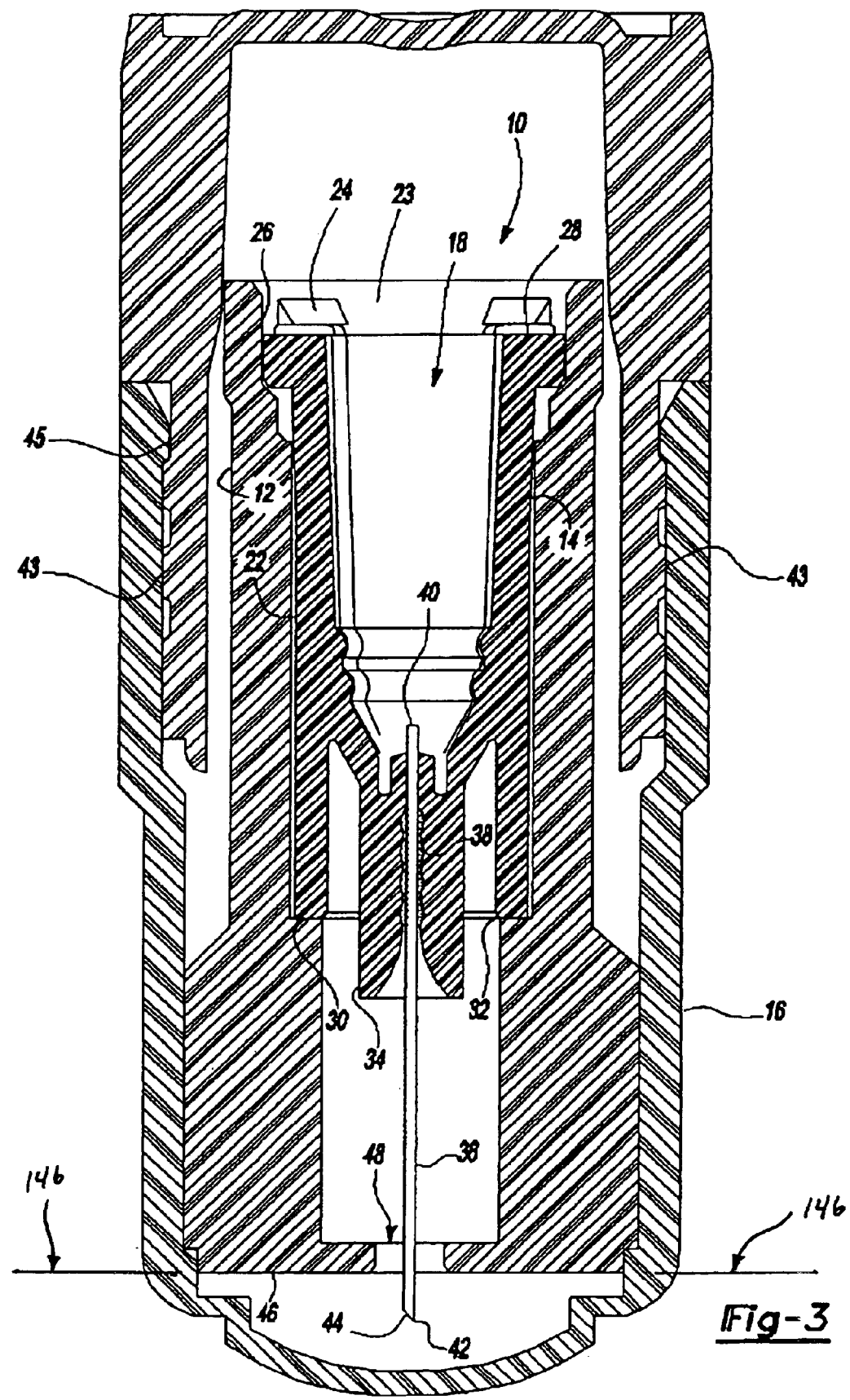
FIG. 3 is a side sectional view of the needle assembly.

Referring to FIG. 3, the limiter portion 12 defines a tubular chamber 22 wherein the hub portion 14 is received. A plurality of snaps 24 are disposed on a wall 23 of the tubular chamber 22 and clasp a flange 26 circumscribing a rearward end 28 of the hub portion 14 thereby securing the hub portion 14 inside the tubular chamber 22. The tubular chamber 22 includes a ridge 30 that abuts a forward edge 32 of the hub portion 14. The forward edge 32 defines the periphery of hub 14. A sheath 34 is centrally disposed to the forward edge 32 upon the hub portion 14. A needle cannula 36 is received by the sheath 34 and defines an axis of the forward edge 32. The needle cannula 36 is fixedly attached to the sheath 34 of the hub portion 14. Preferably, an adhesive 38 fixedly attaches the needle cannula 36 to a sheath 34. More preferably, an epoxy adhesive that is curable with ultraviolet light is used to fixedly attach the needle cannula 36 to the sheath 34. However, other methods of affixing the needle cannula 36 to the sheath 34 may be used such as an interference fit.

The needle cannula 36 includes a rearward needle end 40 that extends through the sheath 34 into the throat 18 of the hub portion 14. When the prefillable container 20 is inserted into the throat 18 the rearward needle end 40 is in fluid communication with the prefillable container 20 thereby allowing the substance disposed within the prefillable container 20 to be expelled through the needle cannula 36. Preferably, the prefillable container 20 will be inserted into the throat 18 just prior to administering the intradermal injection. The rearward needle end 40 may be extended and pointed (not shown) to be able to pierce the sealed prefillable container making the fluid connection. The throat 18 includes a tapered bottom 21 adapted to retain the inserted prefillable container 20 through a Luer Slip connection as is well known in the art of syringe retention. Alternatively, a Luer Lok connection (not shown) may be utilized to retain the prefillable container 20 within the throat 18.

The needle cannula 36 includes a forward tip 42 that is adapted to administer an intradermal injection. Preferably, the forward tip 42 includes a beveled edge 44 ranging in length from approximately 0.8 mm to 1.0 mm. More preferably, the beveled edge 44 includes a length of approximately 0.9 mm. A standard bevel tip length ranges from approximately 1.3 mm to 1.6 mm. The reduced length of the present beveled edge 44 reduces the potential of the needle cannula 36 passing through the dermis layer of the skin of the animal and resulting in the substance from the prefillable container 20 being injected into the subcutaneous region of the animal and conversely also reduces the potential for leakage.

Figures 6A, 6B:
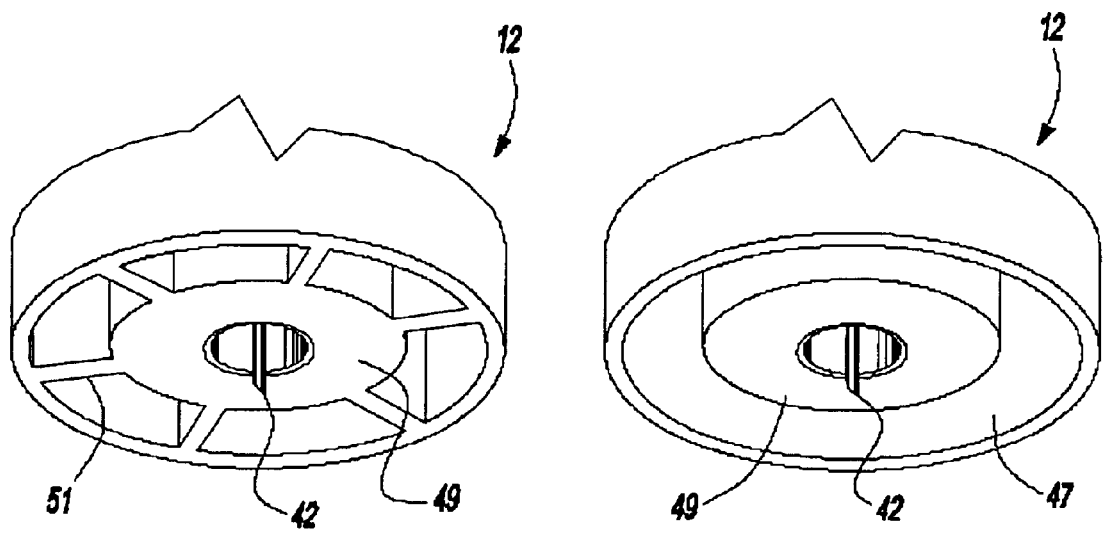
FIG. 6A is a perspective view of an alternative skin engaging surface of the needle assembly.
FIG. 6B is a perspective view of a second alternative skin engaging surface of the needle assembly.

The limiter portion 12 surrounds the needle cannula 36 and extends away from the hub portion 14 toward the forward tip 42 of the needle cannula 36. The limiter portion 12 includes an opening or aperture 48 which closely receives the needle cannula 36 and a generally flat skin engaging surface 46 extending in a plane 146 that is generally perpendicular to the axis of the needle cannula 36 within about fifteen degrees of perpendicular or more preferable within about five degrees. The skin engaging surface 46 is adapted to be received against the skin of the animal to administer an intradermal injection of the substance. The skin engaging surface 46 is represented as being generally flat and continuous and provides for a stable placement of the needle assembly 10 against the animal's skin. Referring to FIG. 6A, the skin engaging surface may include an annular groove 47 with a central surface 49 circumscribing the needle cannula. FIG. 6B shows a skin engaging surface 46 having a plurality of spokes 51 projecting outwardly from the central surface 49 in a plane generally parallel to that of the central surface 49. The skin engaging surface 46 provides stability for the device during injection and preferably has a cross-section of at least 5 mm or between 5 to 20 mm.

The forward tip 42 of the needle cannula 36 extends beyond the skin engaging surface 46 a distance of approximately 0.5 mm to 3.0 mm and preferably about 1.0 to 2.0 mm, and more preferably 1.5 mm±0.2 to 0.3 mm. The length the needle cannula 36 extends beyond the skin engaging surface 46 is determined by the position of the ridge 30 relative to the skin engaging surface 46. Therefore, the limiter portion 12 limits penetration of the needle cannula 36 into the dermis layer of the skin of the animal so that the substance is injected into the dermis layer of the animal. When the hub portion 14 is inserted into the tubular chamber 22 of the limiter portion 12 during assembly, the needle cannula 36 is inserted through an aperture 48 disposed in the skin engaging surface 46 of the limiter portion 12. Thus, only the length of the needle cannula 36 extending through the aperture 48 is available to be inserted into the skin of the animal.

Referring to FIGS. 1A and 1B, the forward cap 16 conceals the forward tip 42 of the needle cannula 36. The rearward cap 17 mates to the forward cap 16 and is removably secured with an interference fit provided by a plurality of annular ribs 43 disposed upon a surface of the rearward cap and abutting the forward cap 16. The forward cap 16 includes an annular protuberance 45 positioned opposite the annular ribs 43 providing a snapping action when the forward cap 16 and the rearward cap 17 are mated. The caps 16, 17 provide a sanitary enclosure for the assembly 10. To ensure the assembly 10 has not been accessed prior to administering the injection, a tamper indicator strip 47 is positioned over a seam formed between the caps 16, 17. The strip 47 is perforated along the seam. A ripped or torn perforation indicates that the assembly 10 has been open and that the needle cannula 36 may no longer be sanitary.

Figure 4:
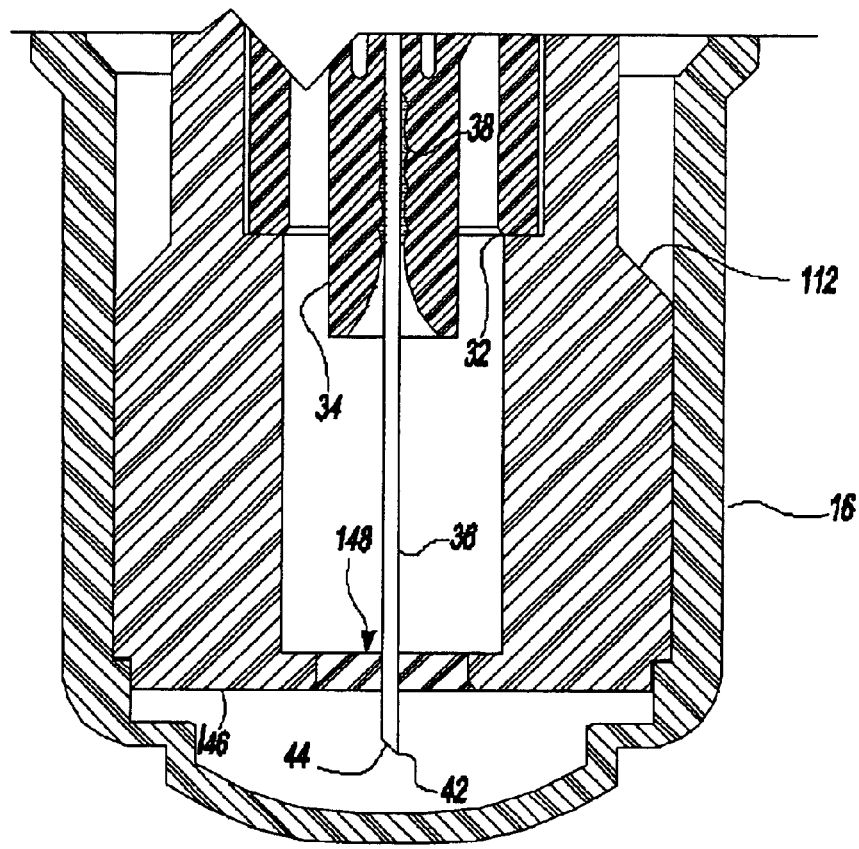
FIG. 4 is a side sectional view of an alternative embodiment of the needle assembly.

An alternative embodiment of the limiter portion 112 is shown in FIG. 4. The alternative limiter portion 112 includes an alternative skin engaging surface 146 having an elastomeric central area 148 functioning as a piercable septum surrounded by a nonelastomeric substrate comprising the remainder of the skin engaging surface 146 and the alternative limiter 112. When the hub portion 14 is inserted into a throat of the alternate limiter 112 the forward tip 42 of the needle cannula 36 pierces the elastomeric central area 148 of the skin engaging surface 146. The elastomeric central area 148 includes a larger diameter than the aperture 48 of the preferred embodiment. Therefore, it should be understood that the assembly process of mating the hub portion 14 with the alternate limiter 112 will be more easily performed because the needle cannula 36 will not have to be inserted through a narrow aperture 48. Further, while administering the intradermal injection, the elastomeric central area 148 provides uniform pressure on the skin of the animal facilitating the formation of a wheal in the skin.

Figure 5:
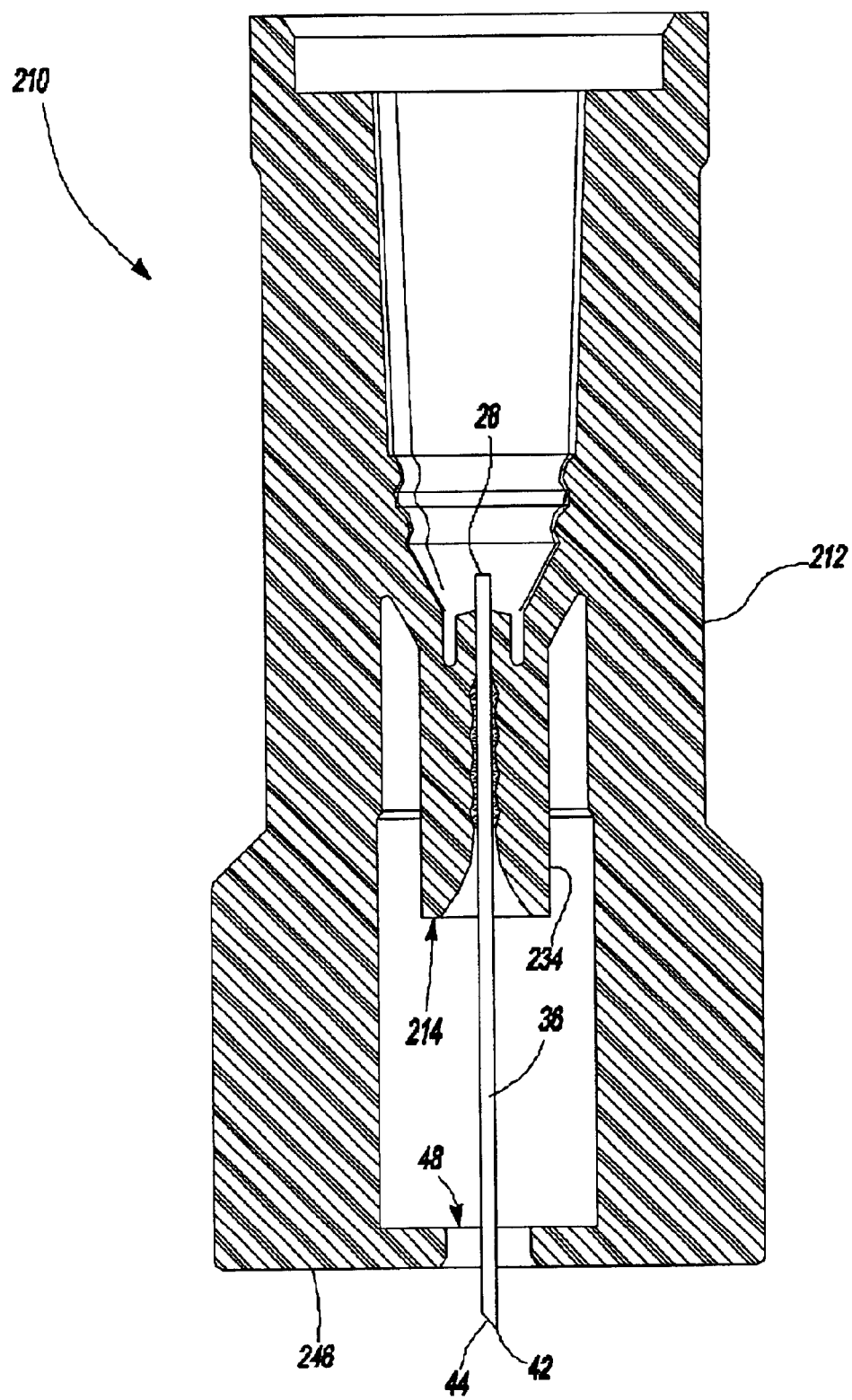
FIG. 5 is a side sectional view of a second alternative embodiment of the needle assembly.

A second alternative embodiment is generally shown in FIG. 5 at 210. In this embodiment, the limiter portion 212 and the hub portion 214 are integrally formed as a single piece. The needle cannula 36 is fixedly attached to the hub portion 214 of the single component 210 behind a skin engaging surface 246 of the limiter portion 212. Preferably, the needle cannula 36 is inserted through an aperture 248 disposed in the skin engaging surface 246. The needle cannula 36 is fixedly attached to a sheath 234 disposed in the hub portion 214 behind the skin engaging surface 246. The needle cannula 36 is affixed through similar means as has been disclosed for the preferred embodiment. Additionally, the rearward end 28 of the needle cannula 36 is disposed in the throat 218 of the hub portion 214 and thereby establishes fluid communication with the prefillable container 20 in a similar fashion as has been disclosed for the preferred embodiment.

Referring to FIG. 7, a third alternate assembly 310 adapted to shield the needle cannula 36 subsequent to administering an intradermal injection is shown. A sleeve 312 generally defining a tube slidably circumscribes the limiter 314. The sleeve 312 includes a skin engaging end 316 that is aligned in generally the same plane as the skin engaging surface 318 when the assembly 310 is prepared for administering the intradermal injection. A rearward end 320 of the sleeve 312 is tapered inwardly towards the axis of the needle cannula 36. The rearward end 320 abuts a rear flange 322 of the limiter 314, which prevents the sleeve 312 from being removed from the limiter 314 in the direction of the prefillable container 20. In this embodiment, an elastomeric tip cap 323 is removably secured to the skin engaging surface 318 and receives the forward tip 42 of the needle cannula 36.

Subsequent to administering the intradermal injection, the sleeve 312 may be manually pulled in the direction of the forward tip 42 of the needle cannula 36 as shown in FIG. 8. The limiter 314 includes a sleeve stop 324, which engages a corresponding contour 326 disposed on an inside surface of the sleeve 312 thereby preventing the sleeve from being removed from the limiter 314. At least one ramp 328 is disposed upon an outer surface of the limiter 314 over which the rearward end 320 of the sleeve 312 slides when the sleeve 312 is moved to cover the forward tip 42 of the needle cannula 36. The ramp 328 locks the sleeve in the extended position and prevents the sleeve 312 from being retracted toward the prefillable container 20 re-exposing the forward tip 42 once the rearward end 320 of the sleeve 312 has been moved past the ramp 328 in the direction of the forward tip 42.

Referring to FIG. 9, a further alternate embodiment of the needle assembly is generally shown at 410. A needle plunger 412 is inserted through the limiter 414 at a generally perpendicular angle to the needle cannula 36. Depressing a pad 416 disposed on a distal end of the needle plunger 412 drives the needle plunger 412 inwardly of the limiter 414. As shown in FIG. 10, needle plunger 412, when depressed, contacts and bends the needle cannula 36 retracting the needle cannula 36 into the limiter 414 thereby shielding the forward tip 42 of the limiter 414 to prevent exposure thereto.

As will now be understood, the intradermal delivery device 10 of this invention includes a needle enclosure means, which encloses or conceals the needle cannula tip 42 following injection and which preferably cannot be retracted to prevent accidental needle contact or reuse. In one embodiment shown in FIGS. 7 and 8, the assembly includes an extendable shield 312, which locks in the extended position, preventing contact with the needle cannula 36. In another embodiment shown in FIGS. 9 and 10, the needle cannula 36 is bent or deformed beyond its elastic limit by needle plunger 412 to permanently enclose the forward tip 42 within the limiter 414.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, wherein reference numerals are merely for convenience and are not to be in any way limiting, the invention may be practiced otherwise than as specifically described.

What is claimed is:

1. An intradermal needle assembly for use with a prefillable container having a reservoir capable of storing a substance for injection into the skin of an animal comprising:
   a hub portion provided on the prefillable container;
   a needle cannula supported by said hub portion and having a forward tip extending away from said hub portion; and
   a limiter portion surrounding said needle cannula and extending away from said hub portion toward said forward tip of said needle cannula, said limiter including a generally flat skin engaging surface extending in a plane generally perpendicular to an axis of said needle cannula and adapted to be received against the skin of the animal to administer an intradermal injection of the substance, said hub portion and said limiter portion being formed as separate pieces, said limiter portion and said needle cannula being non-movable with respect to each other such that said needle cannula forward tip extends beyond said skin engaging surface a distance ranging from approximately 0.5 mm to 3.0 mm and wherein said limiter portion limits penetration of the needle into the dermis layer of skin of the animal so that the substance is injected into the dermis layer of the animal, said limiter portion defining an inner cavity receiving at least a portion of said hub and including an abutment engaging a corresponding structure on said hub portion thereby limiting the length of said needle cannula extending beyond said skin engaging surface.

2. The assembly as set forth in claim 1 wherein said hub portion includes a throat for receiving the prefillable container.

3. The assembly as set forth in claim 2 wherein said needle cannula is fixedly attached to said hub portion.

4. The assembly as set forth in claim 3 wherein said needle cannula is fixedly attached to said hub portion with an adhesive.

5. The assembly as set forth in claim 4 wherein said adhesive comprises an epoxy curable with ultra violet light.

6. The assembly as set forth in claim 5 wherein said limiter portion includes a plurality of snaps engaging said hub portion thereby fixedly attaching said hub portion to said limiter portion.

7. The assembly as set forth in claim 1 wherein said substance includes an influenza vaccine.

8. The assembly as set forth in claim 1 wherein said needle assembly is attachable to a prefillable container with a Luer fit.

9. An intradermal needle assembly for use with a prefillable container having a reservoir capable of storing a substance for injection into the skin of an animal comprising:
   a hub portion having a throat for receiving the prefillable container;
   a needle cannula being supported by said hub portion and having a forward tip extending away from said hub portion;
   a limiter portion surrounding said hub portion and said needle cannula and extending away from said hub portion toward said forward tip of said needle, said limiter portion including a generally flat skin engaging surface extending in a plane generally perpendicular to an axis of said needle cannula and being adapted to be received against the skin of an animal to receive an intradermal injection of the substance, said hub portion and said limiter portion being formed as separate pieces, said limiter portion and said needle cannula being non-movable with respect to each other such that said forward tip extends beyond the skin engaging surface a distance ranging from approximately 0.5 mm to approximately 3.0 mm and wherein the limiter portion limits penetration of said needle cannula into the dermis layer of the skin of the animal thereby injecting the substance into the dermis layer of the animal, said limiter portion defining an inner cavity receiving at least a portion of said hub and including an abutment engaging a corresponding structure on said hub portion thereby limiting the length of said needle cannula extending beyond said skin engaging surface.

10. The assembly as set forth in claim 9 wherein said needle cannula is fixedly attached to said hub portion.

11. The assembly as set forth in claim 10 wherein said needle cannula is fixedly attached to said hub portion with an adhesive.

12. The assembly as set forth in claim 11 wherein said adhesive comprises an epoxy curable with ultra violet light.

13. The assembly as set forth in claim 9 wherein said limiter portion includes a plurality of snaps engaging said hub portion thereby fixedly attaching said hub portion to said limiter portion.

14. The assembly as set forth in claim 9 wherein said substance includes an influenza vaccine.

15. The assembly as set forth in claim 9, wherein said needle assembly is attachable to a prefillable container with a Luer fit.

* * * * *